United States Patent [19]

Brake

[11] Patent Number: 4,588,684
[45] Date of Patent: May 13, 1986

[54] A-FACTOR AND ITS PROCESSING SIGNALS

[75] Inventor: Anthony J. Brake, Berkeley, Calif.

[73] Assignee: Chiron Corporation, Emeryville, Calif.

[21] Appl. No.: 488,857

[22] Filed: Apr. 26, 1983

[51] Int. Cl.[4] ............... C12P 21/00; C12N 15/00; C12N 1/16; C12N 1/00
[52] U.S. Cl. .................. 435/68; 435/172.3; 435/255; 435/317; 935/28; 935/37; 935/69; 536/27
[58] Field of Search ............ 935/23, 28, 37, 47, 935/48, 64; 435/172.2, 172.3, 253, 317, 68, 70, 71; 536/27, 28 R, 29

[56] References Cited

U.S. PATENT DOCUMENTS 4,338,397 7/1982 Gilbert et al. ............... 435/68

OTHER PUBLICATIONS

Kurjan et al., *Cell*, V. 30, pp. 933-943, Oct. 1982, "Structure of a Yeast Pheromone Gene (MFα): A Putative α-Factor Precursor Contains Four Tandem Copies of Mature α-Factor".

Thorner, pp. 160-165, *The Molecular Biology of the Yeast Saccharomyces Life Cycle and Inheritance*, Cold Spring Harbor 1981 Article: "Yeast Pheromones and Mating".

Schekman et al., pp. 361-387, *The Molecular Biology of the Yeast Saccharomyces: Life Cycle and Inheritance*, 1982, Cold Spring Harbor Press Article: "The Secretary Process and Yeast Cell Surface Assembly".

Astell et al., *Cell*, V. 27, pp. 15-23, "The Sequence of the DNAs Coding for the Mating-Type Loci of *Saccaromyces cerevisiae*".

Grantham et al., *Nucleic Acids Research*, May 10, 1980, vol. 8, No. 9, "Codon Frequencies in 119 Individual Genes Confirm Consistent Choices of Degenerate Bases According to Genome Type".

Nasmyth et al., *Cold Spring Harbor Symposium on Quantitative Biology*, 1981, vol. 45(2), pp. 961-981.

Beggs, *Nature*, vol. 275, Sep. 14, 1978, pp. 104-109, "Transformation of Yeast by a Replicating Hybrid Plasmid".

Davis et al., *Nature*, vol. 283, Jan. 1980, pp. 433-438, "The Mechanism of Protein Secretion Across Membranes".

*Primary Examiner*—Thomas G. Wiseman
*Assistant Examiner*—Robin Lyn Teskin
*Attorney, Agent, or Firm*—Bertram I. Rowland

[57] ABSTRACT

Novel DNA constructs are provided for efficient expression of polypeptides by yeasts. The constructs employ yeast a-factor secretion leader and processing signals joined to a DNA sequence encoding a polypeptide of interest in reading frame with the a-factor signals. The constructions provide for the expression, secretion and maturation of the desired polypeptide. A strategy is provided for the isolation of the a-factor secretion leader and processing signals and the joining, by means of a relatively short adaptor, molecules of the DNA sequence encoding the polypeptide to the processing signals in proper reading frame.

The bacterial cell strain *E. coli* HB101 (pAB163) was deposited at the A.T.C.C. on Apr. 20, 1983 and given Accession No. 39342.

11 Claims, 1 Drawing Figure

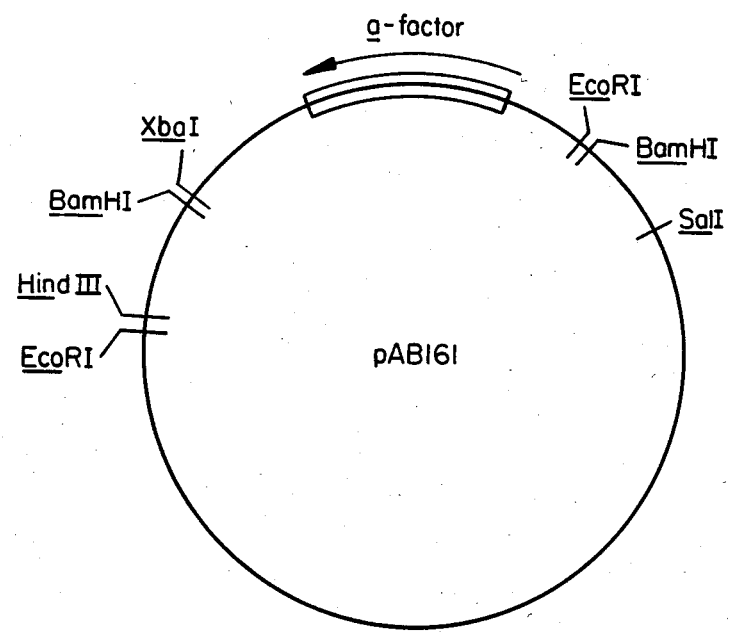
FIG._1.

a-FACTOR AND ITS PROCESSING SIGNALS

BACKGROUND OF THE INVENTION

FIELD OF THE INVENTION

The initial stages of the biological revolution demonstrated the feasibility of obtaining expression of mammalian genes in lower organisms. Because of the much greater amount of knowledge associated with the regulatory sequences of bacteria, bacteria were chosen as the initial host for producing heterologous proteins. However, bacteria have many shortcomings. Not least of these shortcomings is the fact that they produce an enterotoxin which must be completely removed, if the product is to be administered to a mammalian recipient, e.g. as a pharmaceutical agent.

Furthermore, the codons of the heterologous genes will be expressed with relatively low efficiency, since the preferred codons of the source of the heterologous protein and the host will be substantially different. In addition, where the product of interest needs to be processed, such as glycosylated, matured by removal of polypeptide sequences, or assembled, bacteria frequently prove to be incapable or inefficient at these processes. Moreover, for commerical application of genetic engineering technology it would be desirable for ease of subsequent purification if synthesized products were secreted into the growth medium, a process in bacteria of only limited, laboratory scale use. It is therefore desirable to find alternative hosts.

Yeast as a host has many advantages which recommend its use. The commercial fermentation of yeast is well established. Yeast is a eukaryote unlike bacteria, so that it shares greater similarities with mammalian organisms. Yeast are thus capable of many of the processing steps observed in higher organisms and secretion of several natural polypeptides and proteins is known. Furthermore, yeasts do not produce enterotoxins.

It is therefore desirable to provide yeast regulatory signals which may be employed for the efficient production of heterologous proteins in yeast. While the existence of the regulatory signals may be predicted, their isolation, manipulation, and ultimately establishing that the regulatory signals can operate with alien flanking regions in conjunction with a foreign DNA sequence is long and arduous work, requiring well thought out experimental design, careful manipulation, and rigorous proofs of having achieved the intended result at each of the many stages involved.

DESCRIPTION OF THE PRIOR ART

Betz and Duntze, *Eur. J. Biochem.* (1979) 95:469 report the initial isolation and preliminary characterization of mature a-factor peptide and Betz, Manney and Duntze, *Gamete Res.* (1981) 4:571-584 propose an amino acid sequence for the mature a-factor peptide. Kurjan and Herskowitz, *Cell* (1982) 30:933-943 describe a putative a-factor precursor, describe the sequence and postulate a processing mechanism. U.S. Pat. Nos. 4,336,326 and 4,338,397 describe sequences encoding for leaders in prokaryotes. Julius et al., *Cell* (1983) 32:839-852 describe the role of a membrane dipeptidase in the processing of a-factor. See also copending application Ser. No. 457,325, filed January 12, 1983, which is incorporated herein by reference, where such application describes the use of the a-factor leader and processing signals for expression of a heterologous polypeptide.

SUMMARY OF THE INVENTION

Yeast a-factor in combination with its regulatory signals is detected, isolated, and manipulated to provide for joining to a DNA sequence encoding a polypeptide of interest. The resulting construct provides for expression and maturation of the polypeptide with secretion of the polypeptide into the nutrient medium. An experimental design is provided for the manipulation of the yeast a-factor gene to provide for joining of a DNA coding sequence by means of small adaptor molecules to the yeast a-factor leader and processing signals in proper reading frame.

DESCRIPTION OF THE FIGURE

FIG. 1 is a diagram of the plasmid pAB161.

DETAILED DESCRIPTION OF SPECIFIC EMBODIMENTS

In accordance with the subject invention, eukaryotic hosts, particularly yeasts, are employed for the production of secreted, usually mature or maturable, polypeptides, where such polypeptides may be harvested from a nutrient medium. The polypeptides are produced by employing a DNA construct encoding for yeast a-factor secretion leader and processing signals joined in proper reading frame to a DNA sequence encoding for a polypeptide of interest. The resulting construct encodes for a pro-polypeptide, which will contain the signals for secretion of the pro-polypeptide and processing of the polypeptide, either intra- or extracellularly, desirably to the mature polypeptide. Where the pro-polypeptide is incompletely processed, appropriate peptidases, particularly membrane peptidases, may be employed for completing the maturation of the pro-polypeptide. This invention contemplates the production of secreted pro-polypeptide, partially processed pro-polypeptide and mature polypeptide and mixtures thereof.

Constructs of the subject invention will have the following formula defining a pro-polypeptide:

$$((PS)-(\text{a-factor}))_n-PS-\text{gene}$$

wherein:

PS indicates yeast-recognizable processing signals for cleavage and removal of amino acids, the processing signals including at least two basic amino acids, which basic amino acids are lysine and arginine;

a-factor intends the DNA sequence encoding for at least a portion of the mature a-factor, usually the entire a-factor;

n is 0 or 1; and

"gene" intends a DNA sequence other than a-factor having an open reading frame encoding for a polypeptide of interest, which is joined at the terminal base of the immediately preceding PS (the processing signal) in proper reading frame. For the purposes of this invention "gene" encompasses fused proteins, where a structural gene may be inserted into another structural gene in proper reading frame, portions or complete structural genes joined together or arbitrary synthetic sequences having no known natural analog.

For the most part, the DNA constructs of the subject invention will have at least the following formula:

$$L-(PS-(\text{a-factor}))n-PS-\text{gene}$$

wherein:

L intends the yeast a-factor secretory leader sequence, or similar sequence providing for secretion; and
all the other symbols have been defined previously.
PS will for the most part have the following formula:

B—D—F—H wherein:

B and D are the same or different, and define the codons for the basic amino acids lysine and arginine, preferably being AAG; and F and H are the same or different and define the codons for the acidic amino acids, aspartic or glutamic acid or the amides thereof, asparagine or glutamine, preferably being a combination of acid and amide, more preferably, F being GAC and H being AAC. The preferred DNA sequence is the naturally occurring DNA sequence encoding for lys-lys-asp-asn.

Alternatively, PS may have the formula:

$$((B-D)_s-(F-H)_t-(B-D)_v$$

wherein:
s and v are 1–3; and
t and u are 0–3.

Thus, the processing signal may be varied by elimination of the acid amino acids and their amides or increasing the number of basic amino acids or providing for multiple dipeptides or tetrapeptides having the acid amino acid and the amide of the acid amino acid as repetitive dipeptide sequences or having the two basic amino acids in addition. However, for the most part, these additional amino acids will add a further complication to the organization of the construct, and therefore normally will not be used.

The secretion leader sequence of yeast a-factor is relatively short, being about 15 to 20 amino acids, more particularly, about 17 amino acids. The leader sequence has a methionine at its N-terminus.

In order for the polypeptide of interest to be expressed, it will be necessary to prepare a construct which will have a competent replication system and transcriptional regulatory signals for use in yeast. However, to the extent that the secretion and processing signals will be recognized by hosts other than yeast, replication systems for such other hosts may be employed. Usually the construct will include other functional DNA sequences as well, where the function may have been employed during the construction of the construct or may serve a useful function during the expression of the polypeptide.

Constructs can be prepared which are provided with the necessary transcriptional regulatory signals. That is, such constructs will include a RNA polymerase binding site, which may have contiguous or non-contiguous sequences, which binding site may be the wild type for a-factor or may be the RNA polymerase binding site for a variety of other yeast genes, such as the promoters concerned with enzymes involved in the glycolytic pathway, such as phosphoglucokinase, glyceraldehyde-3-phosphate dehydrogenase, pyruvate kinase, phosphoglucoisomerase, triosephosphate isomerase, alcohol dehydrogenase, etc., or with metallothionein, viral promoters, or the like. Reference to these promoters may be found in Hitzeman et al., *J. Biol. Chem.* (1980) 255:12073–12080.

In addition to the promoters, various sequences regulating the promoters may also be employed, such as enhancers and DNA binding sites for repressors, derepressors, activators, and the like. Other DNA sequences which may be involved include ribosomal binding sites, cap sequence, stop codons, transcriptional terminator, etc. One or more of these sequences may be present as part of the construct or may be available as a part of a replication system which may serve as a vector. Usually, the replication system will be associated with other functions to be described subsequently.

The yeast a-factor promoter and leader region may be joined to a yeast replication system, e.g. 2μm plasmid and/or ARS1+CEN3 to provide an expression vector having one or more convenient restriction sites. This expression vector may be formulated as follows:

$$P-L-(PS-(a\text{-factor}))_n-(PS-(gene\ r))_w-|RepS|_q;$$

or more particularly as follows:

$$-RS-P-(cap)_m-(RBS)_p-ic-L'-(PS-(a\text{-factor}))_n-PS-gene-sc-T-|RepS|_q$$

wherein:

PS and gene have been defined previously;

RS intends regulatory signals which may be on either side of P and includes enhancers and DNA binding sites for repressors, derepressors and activators;

P is an RNA polymerase binding site or promoter, particularly the a-factor wild-type promoter;

cap is a capping sequence;

ic is the f-met initiation codon, which is part of the secretion leader sequence;

L' is a DNA sequence which with ic defines the amino acid sequence of the a-factor leader or similar sequence providing for secretion;

sc intends one or more stop codons;

T intends a transcriptional terminator;

|RepS| intends a replication system which may be at any position in the vector external to the immediate expression region of the construct, generally an episomal or viral replication system having other than the wild-type flanking regions;

m, n and p and r are 0 or 1;

q is at least 1 and may be 2 or more, usually 1 to 2;

w is 0 or a small integer, generally 3 or less, with at least one of n or w being 1;

wherein the construct may be linear or circular and except for |RepS| the various sequences are in the order indicated with the promoter directed toward the gene.

The leader secretion sequence will for the most part encode for the following polypeptide sequence:

met-gln-pro-ser-thr-ala-thr-ala-ala-pro-lys-glu-lys-thr-ser-ser-glu

The processing signal sequence will for the most part encode for a polypeptide sequence of the following formula:

| | | asp | asp |
|---|---|---|---|
| lys | lys | asn | asn |
| arg | arg | glu | glu |
| | | gln | gln | where any amino acid in a column may be employed. Of particular interest is the DNA sequence (unless otherwise indicated, sequences will read in the 5'-3' direction):

AAG AAG GAC AAC encoding for the natural processing signal having the following amino acid sequence:

lys lys asp asn.

The cloning and expression constructs will generally be from about 5 to 50 kbp (kilobase pairs), where plasmids will generally range from about 5 to 25 kbp. Where viral vectors are used, packaging requirements may result in constructs of up to about 50 kbp.

One strategy for developing the constructs of this invention is as follows: The DNA sequence encoding for the pro-a-factor can be obtained from the yeast genome by any convenient means, e.g. detection by hybridization with labeled probes. Where the fragment is greater than about 1000 bp, the fragment may be reduced by appropriate cleavage at available restriction sites. Conveniently, within the a-factor gene near the C-terminus of the mature peptide is an AvaII restriction site and the AvaII restricted fragment may be resected, so as to have the terminus of the fragment at a convenient site upstream from and proximal to the first base of the a-factor coding sequence. Preferably, the terminus is in the processing signal sequence, more preferably 29 bases upstream from the AvaII cleavage site. This fragment may then be ligated to linkers having a flush end and a cohesive end, where the linker encodes, by itself or in combination with the terminal bases of the fragment, for an endonuclease recognition site. Particularly, if one resects 29 bases so that the three 3'-terminal bases of the fragment are 5'-AGG, by adding a linker having 5'-CCT, a StuI (5'-AGGCCT-3') site is created, so that one can screen for the desired fragment. In the illustrative example, after addition of the linker and any other appropriate manipulation, e.g. endonuclease digestion, plasmids may then be screened for the StuI site which was created by the linker containing the 5'-sequence CCT which was joined to the 3'-terminal AGG to define the StuI site. The plasmids may additionally be pre-screened, if desired, using a radiolabeled oligonucleotide probe complementary to the desired junction sequence.

A linker is employed which encodes a recognition site for an endonuclease which cleaves away from the recognition site. Furthermore, the asymmetry of the recognition site directs the cleavage upstream, generally about three to fifteen bases upstream from the recognition sequence. In the present example, the recognition site is a HgaI site. The presence of the StuI site ensures that the HgaI cleavage site is in the a-factor secretion leader sequence. With the HgaI cleavage in the a-factor leader region of the gene, the overhang DNA sequence is not a recognition sequence for an endonuclease which would be employed in further construction.

The a-factor leader fragment now contains both StuI and HgaI recognition and restriction sites either of which may be used for further manipulation.

By appropriate selection of restriction enzymes and adaptors, one can provide for linking the leader sequence to a gene through the processing signals, where the gene is in reading phase with the leader sequence, to provide a DNA fragment encoding for the pro-polypeptide. By providing for convenient restriction sites outside of the coding region for the joined leader and gene DNA sequence, one may clone the coding fragment for the pro-polypeptide and transcriptional regulatory signals, if present, in a cloning vehicle and then excise the coding fragment from the cloning vehicle and, as appropriate, insert the fragment into an expression vector in appropriate juxtaposition to the transcriptional regulatory signals. Preferably, and as will be described subsequently, one employs restriction sites, where the transcriptional regulatory signals of the a-factor are retained so that the construct which is inserted into the expression vector does not require the presence of a promoter, although tandem promoters are permissible.

The a-factor leader and processing signals and the strategy described above can be used for the expression of any polypeptide of interest, either derived from yeast or heterologous to yeast. For the most part, the polypeptides of interest will be naturally occurring polypeptides from other than yeast, particularly mammals, more particularly primates, and most frequently domestic animals or human. In addition, synthetic polypeptides may also be of interest.

The construct provides a portable sequence for insertion into vectors where the construct may be joined to include the gene of interest for expression. The resulting replication construct provides a convenient replication system with transcriptional signals as well as secretory and processing signals and having a restriction site which by the use of adaptors allows for insertion of a gene encoding a polypeptide of interest in reading frame with the secretory and processing signals. Thus one can obtain expression of such gene in a host recognizing the yeast secretory signals to produce a secreted processed pro-polypeptide.

The final construct will be an episomal element capable of stable maintenance in a host, particularly a fungal host such as yeast. The construct includes one or more replication systems, desirably two replication systems, which individual replication systems may be a single sequence or non-contiguous plural sequences, allowing for both maintenance in the expression host, particularly yeast, and cloning in a prokaryote. In addition, one or more selection markers may be included, which will allow for selective pressure for maintenance of the episomal element in either or both of the hosts. Furthermore, the episomal element may be maintained at high or low copy number, the copy number generally ranging from about 1 to 200, more usually from about 1 to 100. With high copy number episomal elements, the number of copies will generally be at least 10, usually at least 20, and usually not exceeding about 150, more usually not exceeding about 100 copy number.

Depending upon the particular polypeptide of interest, either high or low copy numbers may be desirable, taking into consideration the effect of the polypeptide product on the host and the efficiency of secretion. Where the presence of the expression product of the gene may have a deleterious effect on the viability of the host, a low copy number may be indicated.

Various hosts, particularly yeast hosts, may be employed, particularly mutants having desired properties, either lesions allowing for complementation, mutants lacking or having specific regulatory systems, or the like. It should be appreciated that depending upon the rate of production of the expression product of the construct, the processing enzyme may or may not be adequate for processing at that level of production. Therefore, a mutant having enhanced production of the processing enzyme(s) may be indicated or enhanced production of the enzyme(s) may be provided by means of an episomal element. Generally, the production of the enzyme should be of a lower order than the production of the desired expression product.

Alternatively, there may be situations where intracellular processing is not desired. In this situation, mutants would be desirable which lack the processing enzymes in their membrane or have relatively inefficient processing. In this situation, the product can be subsequently processed in vitro.

Furthermore, the structural gene may be present as a repeating unit in tandem, with intervening processing signals. The product may then be processed in whole or in part, with the result that one will obtain the various poly(amino acid) sequences either individually or in tandem for subsequent processing. In many situations, it may be desirable to provide for different tandem sequences, where each of the sequences is a subunit of a particular protein product. In some situations it may be desirable to eliminate the processing signals intervening between adjacent tandem heterologous structural genes so as to provide for the production of a multifunctional fusion product.

The structural gene may encode for any type of polypeptide of interest. The polypeptide may be as small as an oligopeptide of eight amino acids or may be 100,000 daltons or higher. Usually, single chains will be less than about 300,000 daltons, more usually less than about 150,000 daltons. Of particular interest are polypeptides of from about 5,000 to 150,000 daltons, more particularly of about 5,000 to 100,000 daltons. Illustrative polypeptides of interest include hormones and factors, such as growth hormone, somatomedins epidermal growth factor, etc.; the endocrine secretions, such as luteinizing hormone, thyroid stimulating hormone, relaxin, secretin, oxytocin, insulin, vasopressin, renin, calcitonin, follicle stimulating hormone, prolactin, etc.; hematopoietic factors, e.g. erythropoietin, colony stimulating factor, etc.; lymphokines, e.g. interleukin-2; globins, globulins, e.g. immunoglobulins, albumins; interferons, such as α, β and γ; regulatory proteins and repressors; enzymes and structural proteins; endorphins, e.g. β-endorphin, enkephalin, dynorphin, mammalian pathogen proteins, e.g. HBsAg, capsid proteins, etc.

Having prepared the episomal elements containing the constructs of this invention, one may then introduce such element into an appropriate host. The manner of introduction is conventional, there being a wide variety of ways to introduce DNA into a host. Conveniently, spheroplasts are prepared employing the procedure of, for example, Hinnen et al., PNAS USA (1978) 75:1919–1933 or Stinchcomb et al., EP No. 0 045 573. The transformants may then be grown in an appropriate nutrient medium and where appropriate, selective pressure maintained on the transformants. Where expression is inducible, one can allow for growth of the yeast to high density and then induce expression. In those situations where although secreted, a substantial proportion of the product may be retained in the periplasmic space, one can release the product by treating the yeast cells with an enzyme such as zymolase or lyticase.

The product may be harvested by any convenient means, e.g. centrifugation and the protein then purified by filtration, chromatography, electrophoresis, dialysis, solvent-solvent extraction, etc.

In accordance with the subject invention, one can provide for secretion of a wide variety of polypeptides, so as to greatly enhance product yield, simplify purification, minimize degradation of the desired product, and simplify the processing equipment and engineering requirements. Furthermore, utilization of nutrients based on productivity can be greatly enhanced, so that more economical and more efficient production of polypeptides may be achieved. Also, the use of yeast has many advantages both in avoiding enterotoxins, which may be present with prokaryotes, and in employing known fermentation techniques, which have been developed for yeast over long periods of time, which techniques include isolation of yeast products.

The following examples are offered by way of illustration and not by way of limitation.

EXPERIMENTAL

Isolation of the a-factor Structural Gene

A collection of oligonucleotides with the following sequences is synthesized:

These oligonucleotides are used to probe by hybridization of a yeast DNA fragment library cloned in the plasmid YEp13 (Nasmyth and Tatchell, Cell (1980) 19:753). This oligonucleotide pool is designed to include molecules complementary to a region of DNA encoding the a-factor peptide, based on the reported structure of the mature a-factor peptide (Betz et al., op.cit., infra). The amino acid sequence of the mature a-factor peptide is reported as:

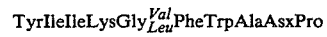

and the oligonucleotide probe extends from the first 5'-base encoding the second Ile through the second base of Asx.

A 19.5 kb plasmid, pAB151, is identified by hybridization to this oligonucleotide pool. Following digestion of pAB151 with the restriction enzymes EcoRI and XbaI, a 1500 bp fragment is identified which contains the hybridization detected segment of DNA. Following repair of the overhanging ends of this fragment with DNA polymerase Klenow fragment and the addition of BamHI oligonucleotide linkers, this fragment is ligated into the BamHI site of plasmid pBR322 to obtain plasmid pAB161, a 5900 bp plasmid. Where the direction of the fragment is determined by the coding direction of the a-factor gene, upstream from the fragment is a SalI fragment, an EcoRI fragment at about the site of the BamHI site upstream from the a-factor and an EcoRI downstream from the downstream BamHI site and the HindIII site proximal to the downstream EcoRI site and intermediate the downstream EcoRI and BamHI sites (see FIG. 1).

Structure of the Putative a-factor Structural Gene

The DNA sequence of the insert in pAB161 is determined and found to consist of 1569 base pairs. A region of this DNA is found to contain nucleotides coding for most of the reported a-factor peptide sequence. This sequence is part of a putative a-factor precursor coding sequence as shown in the sequence on the following page.

```
GAATTCGAGACTCAAAGATGCTGTACCGTTCACGCCGTTTAACGGTGATAGAGAAGCACACCCAAGGTTTACGTTGAAA
GGTTCAGTATACAAGATGACCCATTCATCAAAGATCTTGAGCACAGGAAAGAATTTATTGGTCTGGGTCTTCAACACTGTT
ATGCGTGAACGTGTTGACAGAGGCATTTATGGGTGCTTTAAAACATCAGGAT
AGTGTGCAACGTGGCATAAGCTATGTGAAACCACCTACTCTTTTATTTCTATGTACGCATATACATGCATTCACGATCTGT
TTCAGTGTTCAGAAAAAGGAAATTTACATGTTAAATGAAAACCAGTAATCAGAAAAAACAGTAAGAAACCTAAAATGGTAG
TAATTACCCAAAAAAGGAAATTTACATGTTAAATGAAAACCAGTAAGTAAAAAAATGAAATAGAGTCTTCATATATAAACCGCCAGAA
AGATAAAGATACAGATTCAGTGGTTGCTGAAATCAAGTAAAAAAATGAAATAGAGTCTTCATATATAAACCGCCAGAA
                                                        1
                                                       met
ATGAATTAATGAGAGGGATCTGTAACTGTTTCTCGGATAAAAACCAAAATAAGTACAAAGCCATCGAATAGAAATG
                                              10                             20
gln  pro  ser  thr  ala  thr  ala  ala  lys  pro  glu  lys  ser  ser  glu  lys  asp  asn
CAA  CCA  TCT  ACC  GCT  ACC  GCC  GCT  AAA  CCA  GAA  AAA  AGC  AGT  GAA  AAG  GAC  AAC
tyr  ile  lys  gly  val  phe  trp  asp  ala  cys  thr  val  ile  36   AM
                                                                 ala
TAT  ATT  AAA  GGT  GTC  TTC  TGG  GAC  GCA  TGT  ACC  GTT  ATT  GCT  TAG
ACGTTGTTCTCCCTCCTTATCTTCCTTTCCGCTACCAATATATCATGTTTGTTCGTAATATTTCTTTGTTCGTTGTACC
TAATAATAAATATCCTAAGTAATATATATATATATATATATATATATATATAAAATATTTGATACCCTGCTTTTGGTTATCGTTGTACA
TCCATGCACACGCTCATAAGAATTAGGGTTTCGTGTTTGTACATATGTATATGTGGGATCTTGGATCCTCCTTGTAAACAGGCCTCATAA
AGCTGTCTCTGTGTGCGGGAAGATGTCGTTTCATCGGCTGTCCCTCCTGTATGCATAAAATAATATCCAGTAATTGTCGTCTGTTCGTA
AGAGGGAGGATCTACGGGCAGCGGGGTGTTTGTGCTTTGAACTACTCAACACATAAAATATGCACGGCTACAGTGACTATCGT
CATAATCTGTTTTGTTTATGTGCTTTGAACTACTCAACACATAAAATATGCACGGCTACAGTGACTATCGT
CGCTTTGCCTTTGTCCCTTTAGACTGTCTTTATTGTGAAACACAAGATGAAGCAGAGCTGCCTGTATGGAGGAAGCATAAGTTA
ATGGGGCGACAAAGTTCCCAGCGAGAAACAAGATACTGAACTGACGAAGACCTACGCTACACAAGAAGATAAACACATGCTG
ATATACCTCCAGATATTTGCAGATTAGGATACTGAACTGACGAAGACCTACGCTACACAAGAAGATAAACACATGCTG
GCACAAACATTCAAAAACCACCAGAGCCGTTCTAGA Translated Mol. Weight = 3927.15
```

Biological evidence of two types is obtained that show that the 1500 bp BamHI fragment in pAB161 contains a functional a-factor structural gene:

(1) The plasmid pAB161 is used to probe RNA from S. cerevisiae strains of a haploid, α haploid or a/α diploid mating type. Only cells of the a mating type produce RNA which hybridizes to pAB161. Therefore, the insert in pAB161 encodes an a-specific gene.

(2) The 1500 bp BamHI fragment from pAB161 is ligated into the BamHI site of the high-copy yeast plasmid pCl/1 to obtain the plasmid pAB163. (Plasmid pCl/1 is a derivative of pJDB219 (Beggs, *Nature* (1978) 275:104) in which the region corresponding to bacterial plasmid pMB9 in pJDB219 has been replaced by pBR322 in pCl/1. pCl/1 contains a complete yeast 2 μm replicator, yeast LEU2 gene and complete pBR322.)

pAB163 is introduced into the yeast strain AB101 (a leu2 ura3 his4 trp1) by transformation and selection of Leu+ transformants. These transformants are found to produce at least ten-fold greater amounts of a-factor than does a control strain, as judged by a replica plating bioassay.

In comparison with the amino acid sequence reported by Betz et al. (op.cit., infra), the DNA sequence of pAB161 encodes additional amino acids both amino-terminal and carboxy-terminal to the mature a-factor sequence. Additionally, there is a difference in the order of amino acids corresponding to the carboxyl terminus of the mature a-factor peptide (DNA sequence yields: -TrpAspProAla-; reported peptide sequence: -TrpAlaAsxPro).

Preparation of Constructs

The following was the exemplary procedure for a construct employing human epidermal growth factor as the gene for expression. Plasmid pAB161 is cleaved with AvaII and the resulting fragments are resected with nuclease Bal31 to remove approximately 29 bp from each end. An oligonucleotide with the sequence.

5'CCTGCGTCG3'
3'GGACGCAGCAGCT5' is ligated to the resulting mixture. The ligation mixture is digested with the enzymes BamHI and SalI and fragments of approximately 690 bp are gel isolated. These fragments are ligated to pBR322 which has been digested with BamHI and SalI. The resulting plasmids are screened for molecules hybridizing to a $^{32}$p radiolabeled chemically synthesized oligonucleotide Probe with the following sequence:

5'-GACGCAGGCCTTCTT-3'.

Plasmids so selected are then additionally screened for the presence of a StuI site. Suc molecules are created by the junction of the above oligonucleotide at the desired position of the a-factor gene as shown below:

5'AGTGAAAAGAAGGCCTGCGTCGTCGA3'
3'TCACTTTTCTTCCGGACGCAGCAGCT5'

The resulting molecule now has both a StuI and a HaI recognition site adjacent to the region encoding the a-factor leader of the a-factor precursor. Cleavage with StuI results in cleavage in the a-factor leader region of the gene, as shown below:

5'AGTGAAAAGAAGG3'
3'TCACTTTTCTTCC5'

Alternatively, one may employ HgaI for a-factor leader cleavage to generate the product shown below:

5'AGTGAA3'
3'TCACTTTTCTT5'

Either of these product sequences can then be joined to a DNA molecule containing the gene for human epidermal growth factor derived by cleavage of plasmid p328EGF-1.

The DNA sequence obtained from cleavage of P328EGF-1 with HgaI is as follows:

AACTCCGACTCCGAATGTCCATTGTCCCACGACGGTTACTGTTTGCACGACGGTGTTTGT
GCTGAGGCTTACAGGTAACAGGGTGCTGCCAATGACAAAGCTGCTGCCACAAACA
ATGTACATCGAAGCTTTGGACAAGTACGCTTGTAACTGTGTTGTTGGTTACATCGGTGAA
TACATGTAGCTTCGAAACCTGTTCATGCGAACATTGACACAACAACCAATGTAGCCACTT
AGATGTCAATACAGAGACTTGAAGTGGTGGGAAT
TCTACAGTTATGTCTCTGAACTTCACCACCCTTAACTCT

Ligation of these molecules is carried out with following oligonucleotide adaptor molecules: Either (1) a <u>StuI</u>-<u>HgaI</u> adaptor, 5'ACAAC3'
3'TGTTGTTGAG5' if StuI was employed previously to cleave the a-factor leader; or (2) a <u>HgaI</u>-<u>HgaI</u> adaptor, 5'AAGAAGGACAAC3'
3'CCTGTTGTTGAG5' if HgaI was used; and (3) a <u>HgaI</u>-<u>SalI</u> adaptor, 5'TGAGATGATAAG3'
3'ACTATTCAGCT5'

Cleavage of either of these ligation mixtures with BamHI and SalI yields an 870 bp fragment which is isolated and ligated into pCl/1 digested to completion with the restriction enzymes BamHI and SalI and treated with alkaline phosphatase. This mixture is used to transform E. coli HB101 cells. Transformants are selected by ampicillin resistance and their plasmids analyzed by restriction endonuclease digestion. Plasmid DNA from one selected clone (pYaEGF1) is prepared and used to transform yeast AB102 cells. Transformants are selected by their Leu+ phenotype.

Assay and Characterization of Expression Product

Fifty milliliter cultures of yeast strain AB102 (a, pep 4-3, leu 2-3, leu 2-112, ura 3-52, his 4-580) transformed with the above plasmid pYaEGF1 are grown at 30° in medium lacking leucine to saturation (optical density of 600 nm of 5). Cell supernatants are collected by centrifugation and analyzed for the presence of human EGF using the fibroblast receptor competition binding assay. The assay of EGF is based on the ability of both mouse and human EGF to compete with $^{125}$I-labeled mouse EGF for binding sites on human foreskin fibroblasts. Standard curves can be obtained by measuring the effects of increasing quantities of EGF on the binding of a standard amount of $^{125}$I-labeled mouse EGF. Under these conditions 2 to 20 ng of the EGF are readily measurable. Details on the binding of $^{125}$I-labeled epidermal growth factor to human fibroblasts have been described by Carpenter et al., *J. Biol. Chem.* (1975) 250:4297. Using this assay it is found that the culture medium contains readily measurable quantities of human EGF per liter. The human EGF present in the supernatant, may be subjected to appropriate biochemical analytical methods, e.g. gel electrophoresis, HPLC and amino acid sequence analysis. The results of these procedures further confirm the identity of the product.

For further characterization, human EGF present in the supernatant is purified by absorption to the ion-exchange resin Biorex-70 and elution with HCl 10 mM in 80% ethanol. After evaporation of the HCl and ethanol the EGF is solubilized in water. This material migrates as a single major protein of MW approx. 6,000 in 17.5% SDS gels, roughly the same as authentic mouse EGF (MW ~6,000). This indicates that the a-factor leader sequence has been properly excised during the secretion process. Analysis by high resolution liquid chromatography (microbondapack C18, Waters column) indicates that the product migrates with a retention time similar to an authentic mouse EGF standard.

In accordance with the subject invention, novel constructs are provided which may be inserted into vectors to provide for expression of polypeptides having an N-terminal leader sequence and one or more processing signals to provide for secretion of the polypeptide as well as processing to result in a processed polypeptide product, either mature or capable of being freed of superfluous amino acids. Thus, one may obtain secretion of the pro-polypeptide which then may be subsequently processed in vivo or in vitro to provide for the mature product. In this manner, one can obtain a polypeptide having the identical amino acid sequence to a naturally occurring polypeptide. In addition, because the polypeptide can be produced in yeast, glycosylation can occur, so that a product can be obtained which is identical to or substantially identical to the naturally occurring product. Furthermore, because the product is secreted, greatly enhanced yields can be obtained based on cell population and processing and purification are greatly simplified.

Although the foregoing invention has been described in some detail by way of illustration and example for purposes of clarity of understanding, it will be obvious that certain changes and modifications may be practiced within the scope of the appended claims.

What is claimed is:

1. A DNA construct comprising the yeast leader sequence of a-factor including processing signals and a heterologous gene in reading frame with said leader sequence and processing signals.

2. A DNA construct according to claim 1 of the formula:

$$L-(PS-(a\text{-factor}))_n-PS-gene$$

wherein:

L is the a-factor secretory leader sequence;
PS is the processing signal;
gene is a gene heterologous to yeast; and
n is 0 or 1.

3. A DNA construct according to claim 2, wherein said gene is a mammalian gene or portion thereof.

4. A DNA construct according to claim 2, wherein said gene is a mammalian pathogen gene or portion thereof.

5. A DNA construct of the formula:

$$P-L-(PS-(a\text{-factor}))_n-(PS-(gene)_r)_w--$$
$$|RepS|_q$$

wherein:

P is a promoter recognized by yeast RNA polymerase;
L is the a-factor secretory leader sequence;
PS is the processing signal;
gene is a DNA sequence having an open reading frame in phase with L and PS encoding for a polypeptide heterologous to yeast;
q and w are at least one;
|RepS| is a replication system recognized by yeast and may be located anywhere in the construct external to the immediate expression region defined by P and gene as extremities; and
n and r are 0 or 1, at least one of n or r being 1.

6. A construct according to claim 5, wherein r is 1 and said polypeptide is a mammalian polypeptide.

7. A construct according to claim 5, wherein r is 1 and said polypeptide is a mammalian pathogen gene or portion thereof.

8. A construct according to claim 5, wherein said promoter is a-factor promoter.

9. A construct according to claim 5 wherein said replication system recognized by yeast is the yeast 2 μm plasmid or portion thereof.

10. A construct according to claim 5 wherein q is 2 and further comprising a replication system recognized by bacteria.

11. A method for producing a secreted polypeptide product which comprises:

growing yeast cells containing a DNA construct of the formula:

$$P-L-(PS-(a\text{-factor}))_n-(PS-(gene)_r)_w--$$
$$|RepS|_q$$

wherein:

P is a promoter recognized by yeast RNA polymerase;
L is the a-factor secretory leader sequence;
PS is the processing signal;
gene is a DNA sequence having an open reading frame in phase with L and PS encoding for a polypeptide heterologous to yeast;
q and w are at least one;
|RepS| is a replication system recognized by yeast and may be located anywhere in the construct external to the immediate expression region defined by P and gene as extremities; and
n and r are 0 or 1, at least one of n or r being 1;
whereby said secretory leader sequence, processing signals and gene encoding for said polypeptide are expressed as a fused polypeptide, which is secreted and processed by said yeast cells.

* * * * *